United States Patent [19]

Baughman et al.

[11] 4,289,498
[45] Sep. 15, 1981

[54] ONE-STAGE PROTHROMBIN ASSAY AND COMPOSITIONS USEFUL THEREIN

[75] Inventors: D. Joseph Baughman, Flemington; Ann Lytwyn, New Brunswick, both of N.J.

[73] Assignee: Ortho Diagnostics, Inc., Raritan, N.J.

[21] Appl. No.: 1,500

[22] Filed: Jan. 8, 1979

[51] Int. Cl.³ .......................................... G01N 33/86
[52] U.S. Cl. ................................ 23/230 B; 23/918; 252/408
[58] Field of Search ................ 23/230 B, 918; 356/39; 252/408

[56] References Cited

U.S. PATENT DOCUMENTS

| | | | |
|---|---|---|---|
| 3,486,981 | 12/1969 | Speck | 23/918 |
| 3,884,896 | 5/1975 | Birger et al. | 260/112.5 |
| 3,886,136 | 5/1975 | Claeson et al. | 260/112.5 |
| 4,047,890 | 9/1977 | Eichelberger et al. | 23/230 B |
| 4,061,625 | 12/1977 | Thuresson | 260/112.5 |

OTHER PUBLICATIONS

H. C. Hemker, et al., Thrombosis et Diathesis Haemorrhagica 13, 156–175 (1965).

Primary Examiner—R. E. Serwin
Attorney, Agent, or Firm—Geoffrey G. Dellenbaugh

[57] ABSTRACT

A one-stage prothrombin assay which measures the exponential rate of thrombin production in thromboplastin-treated, recalcified plasma. A serum reagent reduces the lag time before thrombin production substantially to zero for both normal and abnormal plasma, thus allowing measurements to be made in just a few minutes.

21 Claims, 10 Drawing Figures

Fig.6.
CHANGE IN OPTICAL DENSITY/TIME

Fig.7.
CHANGE IN OPTICAL DENSITY/TIME AT TIME T

Fig.8.
OPTICAL DENSITY

Fig.9.
OPTICAL DENSITY AT TIME T'

Fig.10.

ONE-STAGE PROTHROMBIN ASSAY AND COMPOSITIONS USEFUL THEREIN

BACKGROUND OF THE INVENTION

1. Field of the Invention

This invention relates to improvements in obtaining medical diagnoses and in particular to a novel one-stage prothrombin assay.

2. Description of the Prior Art

The clotting of blood requires the participation of approximately thirteen clotting factors in a sequence of reactions whereby certain factors are in turn activated by preceding factors or a combination of preceding factors, often in conjunction with various accessory factors such as calcium ion and negatively charged phospholipid bilayer surface. It is known that clotting proceeds by at least two pathways: the so-called extrinsic and intrinsic pathways. The former is initiated by the release of thromboplastin from damaged tissue, while the latter is initiated by contact activation of Factor XII. Both pathways can be accelerated by a feedback loop via thrombin activation on at least Factors VIII and V. The clotting mechanism is represented in simplified form by the following diagram A, in which Roman numerals identify the various clotting factors.

Diagram A

In order to screen for deficiencies in blood factors of either genetic or disease origin and to monitor anticoagulant therapy, three common tests are employed. All three tests measure the time required for the clotting of a patient's plasma upon addition of certain reagents. Each test determines the effectiveness of a portion of the clotting mechanism and thus allows judgements with respect to the effectiveness of the blood factors involved in the studied portion or with respect to the result of anticoagulant therapy.

The first test is the partial thromboplastin time test (PTT), which evaluates the intrinsic pathway. The second test is the one-stage prothombin time test (herein "prothrombin time" or PT), which evaluates the extrinsic pathway. The third test is the thrombin time test (TT), which evaluates that portion of the clotting mechanism subsequent to thrombin production, which is generally dependent upon both fibrinogen concentration and fibrin polymerization. The collective results of these three tests, together with repetitions of the tests in substitution studies (if necessary) allow determination of precise factor deficiencies. It should be noted that a prolongation of the thrombin time invariably also leads to a prolongation of both the partial thromboplastin time and the prothrombin time as currently measured, since a defect subsequent to thrombin production prolongs clotting time regardless of how the clotting mechanism is initiated. A significant deficiency in this portion of the clotting mechanism is, however, quite rare compared to deficiencies in other clotting factors.

The above discussion having been presented as a general background in the mechanism of coagulation, attention will now be focused on the prothrombin time test.

The prothrombin time test is a valuable and widely used diagnostic tool employed to monitor oral anticoagulant (e.g., dicoumarol) therapy and to screen for genetic or disease-caused deficiencies in blood factors I, II, V, VII, and X. This test, as with the other two clotting time tests, is based upon the length of time required for a patient's plasma to clot under the influence of certain reagents—for the PT test these reagents are calcium ion and thromboplastin. The process is illustrated schematically as follows (Diagram B):

Diagram B $$\text{Prothrombin (II)} \xrightarrow[\text{Thromboplastin}]{\text{Ca}^{++}, \text{clotting factors}} \text{Thrombin}$$

$$\text{Fibrinogen (I)} \xrightarrow{\text{Thrombin}} \text{Fibrin Clot}$$

It can thus be seen that the prothrombin time is a function of the times required for the two processes depicted above. The first of these times is the thrombin generation time, that is, the length of time required for the formation of effective amounts of thrombin from prothrombin. The second time is the gelation time, that is, the time required for the actual clot to form once sufficient thrombin is present to promote the reaction of fibrinogen to fibrin. The gelation time is negligible in the presence of excess thrombin concentration compared to fibrinogen concentration for a fibrinogen-normal individual (as defined below). The prothrombin time test is sensitive to only major defects in the second step in Diagram B, due to the large excess of thrombin produced.

The prothrombin time test as presently performed measures the time required for the occurrence of a physical event—clotting, which is to be distinguished from a measurement of chemical concentration or rate. A variety of physical phenomena have been recognized in the art as endpoints for clotting time tests, such as turbidity (of various degrees), precipitates, appearance of strands, change in surface tension, and the like. A variety of instruments have been developed, using different endpoint recognition criteria, so that measurements among instruments are not readily comparable. Moreover, the prothrombin time measurement of the prior art does not lend itself very well to automation, which is a highly desirable objective in modern day diagnostic medicine. While there are instruments for determining prothrombin time which are fully automated, these are generally based on a turbidity measurement to evaluate the formation of a clot and provide a measurement expressed in terms of time.

A further practical difficulty with the current prothrombin time test is that thromboplastin form various commercial sources does not always yield comparable results with the same plasma samples. That is, one cannot quantitatively predict the PT times for a group of plasma samples using thromboplastin from one source based on PT times obtained for the same group of plasma samples using thromboplastin from another source. In other words, it is not possible (for a group of plasma samples) to correlate quantitative PT test results using one source of thromboplastin with those using another source of thromboplastin. This lack of correlatability is recognized in the art as a serious deficiency with the conventional prothrombin time test.

In a typical prothrombin time test as it is currently performed, 0.2 ml of thromboplastin containing calcium ions is added to 0.1 ml of citrated plasma, and the time interval from the moment of addition to the first indication of a clot is measured. Prothrombin times for normal plasmas range from 10 to 14 seconds depending on the laboratory and the particular method employed. For example, optical density instruments tend to give times of 10-11 seconds while manual methods and measurements on a Fibrometer brand clotting instrument tend to give 12-14 seconds for normal plasmas. Clotting times higher than these indicate that the plasma has a deficiency in concentrations of fibrinogen (Factor I), prothrombin (Factor II), Factor V, Factor VII, or Factor X, or a combination of these. This abnormal condition may be caused either by genetic deficiency, by disease, or by anticoagulant therapy. The term "abnormal plasma" as used herein specifically includes plasma of individuals undergoing anticoagulant therapy, as well as those having deficiencies of pathological or genetic origin.

For example, patients to whom heparin (a direct anticoagulant) is being administered may have lengthened clotting times because heparin accelerates the inhibition of thrombin formation and therefore slows down the fibrinogen-to-fibrin reaction catalyzed by thrombin. On the other hand, indirect anticoagulants such as coumarin and dicoumarol inhibit the synthesis of Factors II, VII, and X. (Factor IX is also inhibited by these indirect anticoagulants, but this factor is not part of the extrinsic pathway initiated by thromboplastin.) The subnormal quantities of any of these non-thrombin factors in turn inhibit thrombin formation with consequent reduction in the fibrin clotting reaction and prolonged times in the prothrombin time test. Prothrombin times for abnormal plasma can be as long as about 60 seconds as the test is currently performed.

It is now known that at least the portion of the coagulation mechanism which is common to both the intrinsic and extrinsic pathway proceeds by proteolytic action in which prothrombin is cleaved by a combination of activated Factors V and X in combination with calcium ion and a negatively charged phospholipid bilayer surface to produce thrombin and other fragments. Thrombin in turn acts as a proteolytic enzyme to cleave fibrinogen into fibrin, and a clot is formed.

Knowledge of the mode of action of these clotting factors has led to the development of chromogenic substrates for their determination. These chromogenic substrates are materials which are acted upon and cleaved by certain clotting factors with the resultant production of a colored material; hence the name "chromogenic" (color producing) "substrate" (material acted upon by an enzyme). Since the substrate is designed so that the absorbance maximum for the uncleaved substrate is distinctly different from that of the chromophore released by cleaving process, the determination of the concentration of the cleaving clotting factor reduces to a simple absorbance measurement either at the maximum absorption point of the cleaved chromophore or some other convenient distinguishing wavelength.

These chromogenic substrates generally comprise a polypeptide portion and a chromophore portion; the polypeptide portion can be tailored to be specific to a desired clotting factor, which will then cleave the substrate between the chromophore and the peptide, thus releasing the chromophore. The chromophore is typically p-nitroaniline (pNA) but may also be any of a variety of other materials such as 4-methoxy-$\beta$-naphthalene, 4-methoxy coumarin, 4-trifluoromethyl coumarin, and the like. Polypeptide portions which may be used for the detection and thrombin include L-phenyl-alaninyl-L-pipecolyl-L-arginyl, L-phenylalaninyl-L-valyl-L-arginyl, glycyl-L-prolyl-L-arginyl, and the like. The amino terminus of the polypeptide portion is usually blocked by a blocking group, such as benzoyl, carboxyl, tosyl, a D-amino acid residue, or the like, while the chromophore is attached to the carboxyl terminus. Included within the term "chromogenic substrates" are those materials wherein the cleaved chromophore is detected by its emission spectrum (e.g., fluorescence) such as 4-methoxy-$\beta$-naphthalene, as well as those wherein the cleaved chromophore is detected by its absorbance spectrum such as p-nitroaniline. Chromogenic substrates are known which are specific for thrombin.

Despite the existence of chromogenic substrates for the detection of thrombin, no practical method using these substrates for the evaluation of the single-stage prothrombin time is known. It is believed that this lack is occasioned by following heretofore unsolved problems.

In order to employ the chromogenic substrate in the evaluation of (e.g.) prothrombin time, it is necessary to use a highly diluted test plasma. Otherwise, the formation of the clot totally obscures the color production and renders impossible the measurement of any color change. Moreover, the color produced in undiluted plasma would be too intense for meaningful measurement of color change to be made. If dilute plasma is used, an abnormal prothrombin time can extend to as long as ten minutes or longer, while a normal prothrombin time is extended to about 1-2 minutes. These thrombin generation times are too long to be of practical use, especially in an automated determination method. They are also too disparate in length to both be conveniently measured on the same commercially-available spectrophotometer because of the built-in limitations of such instruments. While it is recognized that some improvements have been made in this area, nevertheless, the determination of prothrombin times using chromogenic substrates has not heretofore been practically possible.

SUMMARY OF THE INVENTION

There is provided by the present invention a new prothrombin assay which allows the benefit of totally automated, accurate determination of the one-stage prothrombin time for "fibrinogen-normal" individuals (as defined below) in a short and comparable time for both normal and abnormal plasma. The subject assay (in contrast to the prior art) is correlatable for different thromboplastin sources. The invention comprises not only the aforesaid method, but also compositions for use in the method. The invention further comprises a method for evaluation of the efficacy of a portion of the blood clotting mechanism.

The method of the invention in its broadest aspect stems from the discovery by the inventors that the exponential rate of thrombin production in thromboplastin-treated, recalcified plasma is a constant for an individual plasma sample, whether normal or abnormal. It has thus surprisingly been discovered that the length of time required for thrombin development, previously thought by those skilled in the art to be the critical element of any prothrombin assay, is indeed irrelevant. All that is necessary for the evaluation of the present prothrombin assay is the slope of the logarithmic plot of thrombin production versus time.

Since the subject method is based on the measurement of thrombin production, any deficiencies in the blood clotting mechanism which are subsequent to thrombin production will not be detected (See Diagram B, above). Since the gelation time (the time required for the second process in Diagram B) is negligible for the vast majority of individuals, the measurement of the exponential rate of thrombin production will correlate with the conventionally measured PT time. For certain individuals, however, who have prolonged PT times due solely to a deficiency in the blood clotting mechanism subsequent to thrombin production, the measurement of the exponential rate of thrombin production will not correlate with the conventionally measured PT time. Individuals whose PT times are prolonged solely due to a deficiency in the blood clotting mechanism subsequent to thrombin production are termed herein "fibrinogen-deficient" individuals, regardless of whether such defect resides in concentration or quality of fibrinogen, the polymerizability of fibrin, or any other aspect of this portion of the mechanism. Individuals not having such a PT time prolonging deficiency are termed herein "fibrinogen-normal" individuals, which is intended to mean that the entire portion of the blood clotting mechanism subsequent to thrombin production is sufficiently normal that no prolongation of the PT time is caused thereby. It should be understood that the conventionally-determined PT time is sensitive only to gross deficiencies subsequent to thrombin production.

The subject method therefore allows a simple determination of the effectiveness of that portion of the blood clotting mechanism measured by a one-stage prothrombin time test, excluding fibrinogen, for any individual, whether fibrinogen-normal or fibrinogen-deficient. This determination is accomplished by determining the exponential rate of thrombin formation in a mixture comprising effective thrombin-forming concentrations of thromboplastin, calcium ion, and test plasma and comparing this determined rate to a compilation of rates for plasmas of known clotting properties. This mixture may also contain a lag-time-reducing concentration of serum reagent.

While the present method is illustrated below by use of a chromogenic substrate as the means whereby the exponential rate of thrombin production is detected, it should be understood that the method is not limited thereto. In its broadest aspect, the present method can be practiced using any means for detecting the rate of thrombin production, including immunoassay (isotopic and non-isotopic), spectrophotometric detection, radioisotope labeling, electrochemical detection, and the like.

Once the exponential rate of thrombin production is determined, reference can be made to a standard curve (more fully described below) to correlate this rate with conventionally-determined one-stage prothrombin times for fibrinogen-normal individuals. Alternately, it is contemplated that such conversion into a time value will be unnecessary when sufficient experience with the present method has allowed preparation of a compilation of normal and abnormal thrombin production rates for a variety of plasmas. The term "compilation" as used herein includes tables, graphs, computer data bases, and the like. Using the present method, normal plasma samples have been found to exhibit an exponential rate of thrombin formation (a) under the conditions of Example III of from about 0.20 to about 0.30, while abnormal plasma samples exhibit an exponential rate of thrombin production less than about 0.20 under the same conditions. The lowest exponential rate obtained to date for an abnormal plasma under the conditions of Example III is about 0.02. It should be understood that the 62 plasmas of Example III represent only a small sample of possible plasma types. It is quite possible that normal plasmas may be found having an exponential rate of thrombin production greater than 0.30 and abnormal plasmas may be found having an exponential rate of thrombin production less than 0.02, all under the conditions of Example III. This summary of results obtained using the present method is an example of a compilation of rates for plasmas of known clotting properties.

To aid in understanding this radical departure from the prior art, reference to the drawings will now be made.

DETAILED DESCRIPTION OF THE INVENTION

Figures 1, 2, 3:
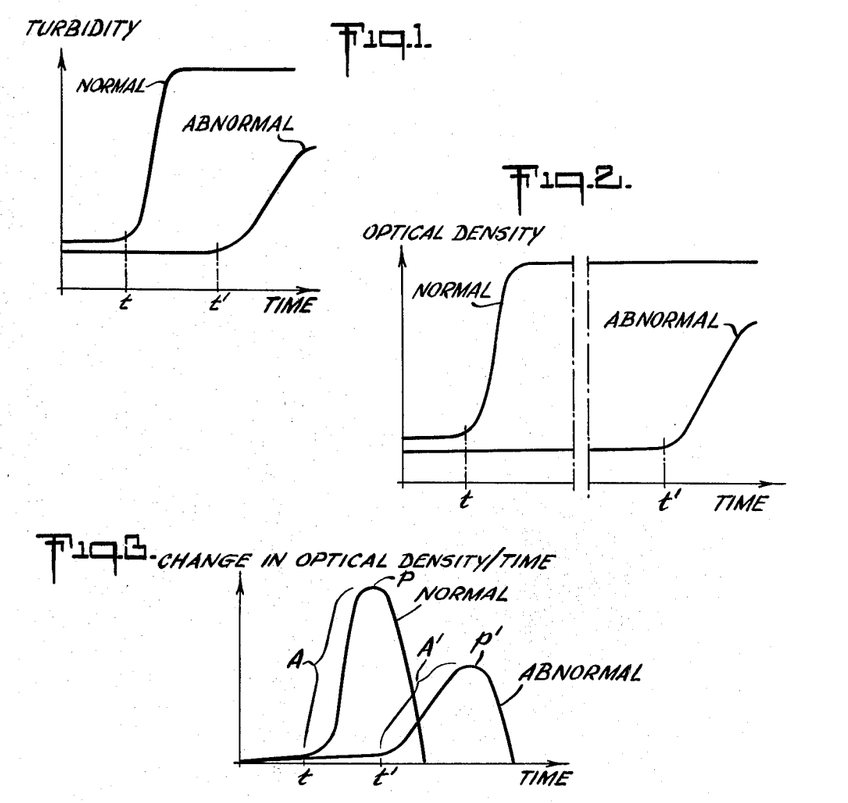
FIG. 1 represents plots of typical prothrombin times using the prior art technique of adding citrated plasma to thromboplastin plus calcium ion.
FIG. 2 represents plots of typical prothrombin times using diluted plasma and a chromogenic substrate for detection.
FIG. 3 represents the derivatives of the curves in FIG. 2.

FIG. 1 represents a plot of typical prothrombin times using the prior art technique of adding citrated plasma to thromboplastin plus calcium ions. After an initial time represented by the distance to t for a typical normal plasma and to t' for a typical abnormal plasma, the turbidity increases due to clot formation. The one-stage prothrombin times are represented by t and t' for the two plasmas. As discussed above, typical prothrombin times for normal plasmas are 10 to 14 seconds, while typical prothrombin times for abnormal plasmas are as high as about 60 seconds. The difficulty of accurately determining the time at which the increase in turbidity begins can be appreciated from an examination of this figure.

FIG. 2 represents a plot of prothrombin times following all the teachings of the prior art but using a chromogenic substrate for the detection of the prothrombin time. In this instance, it should be understood that the plasma has been considerably diluted from the plasma used in the measurement plotted in FIG. 1 in order to allow the detection of the color change. Since the prothrombin time is a function of the plasma concentration, diluting the plasma will increase the time for both normal and abnormal plasma. However, the time increase for abnormal plasma is much greater than that for normal plasma. In FIG. 2 is plotted the observed optical density at a conveniently measured absorbance wavelength of the cleaved chromophore of the chromogenic substrate as a factor of time. There is a time interval called the "lag time" during which no change in color occurs. This time is represented by the distance to t (for normal plasma) and to t' (for abnormal plasma) and corresponds to the prothrombin times measured in FIG. 1 (greatly lengthened due to the plasma dilution). As described above, however, it is impractical to measure prothrombin times using chromogenic substrates in this fashion because of the great length of the lag time for abnormal plasma (up to as much as 10–20 minutes) and the disparity between this time and the time for normal plasma (about 1–2 minutes). Because of the belief in the art that the determination of the rate of clotting necessitates the measurement of the time for clot formation (the "prothrombin time"), the difficulties just recited have made it appear impractical ever to employ chromogenic substrates for a one-stage prothrombin time assay.

It has now been discovered that if the change in optical density with time is plotted versus time, the exponential slope of a portion of this curve can be linearly correlated with the conventionally measured prothrombin time for fibrinogen-normal individuals. This discovery is represented in FIG. 3, in which the derivatives of the curves in FIG. 2 with respect to time are plotted. The lag times t and t' (during which no change in color occurs) correspond to the same times as in FIG. 2. The portions of the curves indicated by the brackets labeled A and A' (sometimes referred to herein as the "burst") depict the rapid increase in optical density due to the rapid rate of initial thrombin production. This burst extends from the end of the lag time (t or t') to the peak of the burst indicated by the letters P and P'. The curves drop off sharply after the peaks due to depletion of the supply of chromogenic substrate.

The portion of the plot in FIG. 3 indicated by the bracket labeled A may be represented by the expression $e^{at}$, where "e" is the base of the natural or Naperian logarithms, "a" equals a constant which is the exponential rate of thrombin production, and "t" equals the elapsed time. Likewise the portion A' may be represented by the expression $e^{a't}$. As used herein, the term "slope" of the portion of a curve such as that designated by the bracket labeled A is defined to mean the constant a. It has been discovered that this slope (which is the exponential rate of thrombin production) can be correlated to the conventionally-determined prothrombin time for fibrinogen-normal individuals. Since the present method measures the rate of thrombin production directly without measuring the time for formation of a fibrin clot, fibrinogen-deficient individuals (as defined above) will not be detected thereby. Hence the results of the present method cannot be correlated with conventional prothrombin times for such individuals. However, since such individuals are extremely rare and moreover can be readily detected by the thrombin time test, this minor disadvantage is seen to be greatly outweighed by the present method's advantages.

It should be understood that the relationship depicted in FIG. 3 holds no matter what means is employed for detection of thrombin production. Thus, while a chromogenic substrate is given as an example of a detection means, the present invention is not intended to be so limited.

Figure 4:
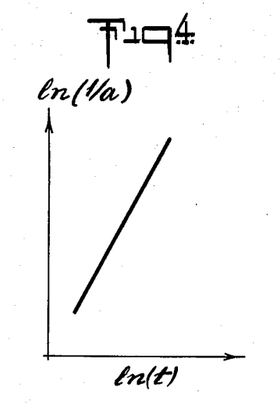
FIG. 4 represents a plot of ln (1/a) vs ln (t).

FIG. 4 represents a plot of the natural logarithm of the reciprocal of the slope versus the natural logarithm of the conventionally-determined prothrombin time. As can be seen from the figure, this relationship is linear. Hence, this standard curve allows correlation of the slope measured from FIG. 3 (or FIG. 6 discussed below) with prothrombin times measured by prior art methods for fibrinogen-normal individuals. This plot may be prepared by measuring the slope in the present method and the PT by a prior method for a number of plasma samples, and graphing the results as shown. Other logarithms (e.g., to base 10), may also be employed for preparation of such a standard curve.

While the use of such a standard curve is helpful to relate the results of the present method to those of prior art methods, it is expected that experience using the present method will decrease reliance on such a curve. In such a situation, the results of the present method for an individual plasma sample may be evaluated by comparison with a compilation of results for a range of plasmas.

Figure 5:
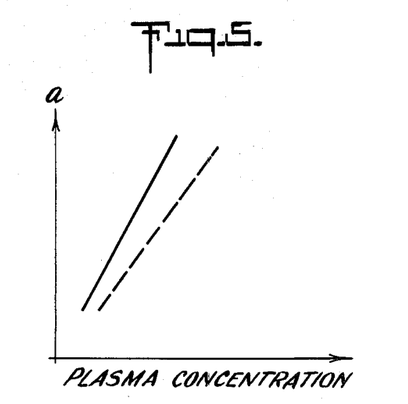
FIG. 5 represents a plot of a vs plasma concentration.

FIG. 5 represents a plot of the slope versus the plasma concentration (solid line), from which it is apparent that this relationship is also linear and allows correlation of these two factors. The dotted line represents the same plot for the same plasma samples but for thromboplastin from a different source. Both plots are linear, allowing correlation of slope values obtained using thromboplastin from any source.

The discovery of this mathematical relationship by Applicants provided stimulus for the further discovery of means whereby the lag time prior to thrombin production for both normal and abnormal plasmas can be considerably reduced so that it is possible, using the method of the invention, to determine the one-stage prothrombin time for normal or abnormal plasma in commercially available equipment in a matter of a few minutes. It is thus apparent that Applicants have provided for the first time a practical, easily automated method for accurately determining the one-stage prothrombin time.

The means for effecting this substantial elimination of the lag time is an activated form of a plasma factor essentially free of prothrombin, identified herein as the "serum reagent." While it is not yet completely understood exactly what this serum reagent is, it can be obtained in at least the following ways. It was first found in normal human serum, the term "serum" having herein the meaning of the supernatant over ordinary clotted human blood. It has also been found that the supernatant serum over clotted plasma produced by treating citrated human plasma with effective clotting concentrations of calcium ion and thromboplastin also contains the serum reagent. However, if no thromboplastin is added (i.e., only calcium ion is added to citrated plasma), a clot will form but the supernatant material will not contain the serum reagent. If an effective clotting concentration of activated Thrombofax (a reagent manufactured by Ortho Diagnostics, Inc.) and calcium ion are added to citrated human plasma, the supernatant left above the clot which forms does contain the serum reagent. However, if thrombin is added to citrated human plasma, the supernatant above the clot which forms does not contain the serum reagent. The presence or absence of serum reagent in the supernatant serum was determined by performing the subject method and observing the degree of reduction in the lag time prior to thrombin formation. Activated Thrombofax is a clot-inducing phospholipid reagent which is a substitute for platelet suspensions to stimulate the intrinsic pathway. The preparation of this class of reagents is described in, for example, W. N. Bell and H. G. Alton, *Nature* (London), 174, 880 (1954).

While it has been found that treatment of nine parts human plasma with either 0.33 parts 0.28 M calcium chloride and 0.67 parts Ortho Brain Thromboplastin (containing 0.01 M calcium ion) or 0.67 parts 0.15 M calcium chloride and 0.33 parts activated Thrombofax will produce supernatant serum containing the serum reagent, it should be understood that considerable variation may be made in these proportions provided that the supernatant serum is essentially free of prothrombin. Determination of the absence of prothrombin and presence of serum reagent in the supernatant serum may easily be accomplished as described herein.

Applicants believe, without wishing to be bound thereby, that the serum reagent is an activated form of Factor VII essentially free of prothrombin. This serum reagent appears to have the effect of priming the feedback loop through the extrinsic pathway referred to above and thus substantially eliminates the lag time (for both normal and abnormal plasma) before the production of significant amounts of thrombin begins. The preferred method of obtaining the serum reagent is to treat citrated human plasma with calcium ion and thromboplastin and remove the supernatant (the serum), which is used as such or may be frozen or lyophilized for storage.

The phrase "essentially free of prothrombin" means that no increase in thrombin generation (measured, for example, using a chromogenic substrate) occurs when the serum containing the serum reagent is treated with thromboplastin and calcium ion. If the serum were not essentially free of prothrombin, treatment with thromboplastin and calcium ion would cause a marked increase in thrombin generation.

Addition of serum (containing serum reagent) to a test plasma, along with calcium ion, thromboplastin, and a means for detecting thrombin production, reduces the lag time for both normal and abnormal plasmas to substantially the same small value, whereby the exponential rate of thombin production and hence the one-stage prothrombin time may be determined in only a few minutes.

It has been discovered that the lag time may also be significantly reduced by addition of an effective lag time reducing amount of thrombin to the test plasma in place of serum reagent, although this is less preferred. A final thrombin concentration of from about 0.05 to about 0.10 units/ml has been found to be effective to reduce the lag time, although not to the minimum value which is preferred. It is contemplated that the final concentration of thrombin for reduction of lag time may be varied somewhat outside the values given above, although the concentration should not be increased to that amount which will clot the mixture.

In the practice of a preferred embodiment of the method of the present invention, there are combined together at a controlled temperature effective concentrations of the following five materials: a chromogenic substrate specific for thrombin, thromboplastin, calcium ion, the serum reagent, and the test plasma. The term "effective concentrations" means the concentrations of thromboplastin, calcium ion and test plasma effective to promote rapid thrombin formation, that concentration of serum reagent (or thrombin) effective to reduce to a minimum the lag time for both normal and abnormal plasma, and that concentration of chromogenic substrate effective to detect thrombin formation during the test period. The mixture of materials is placed into a temperature-controlled spectrophotometer cell and absorbance measurements at the appropriate wavelength effective for detecting the cleaved chromophore are made at various times, preferably by means of an automatic recorder. This measurement is conveniently made at the wavelength at which the absorbance maximum of the cleaved chromophore occurs, but other wavelengths suitable for chromophore detection may also be used. A graphical representation of the change in optical density (absorbance) with respect to time is plotted versus time from which the slope of the curve is obtained using the formula $e^{at}$, where e, a, and t are as previously defined. This slope (a) may be correlated with the conventional prothrombin clotting time test as indicated in FIG. 4.

Figure 6:
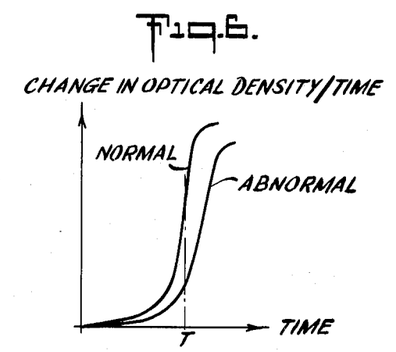
FIG. 6 represents a plot of the change in optical density with time vs time for the present method.

The result of this embodiment of subject method as illustrated in FIG. 6, which represents for a normal and an abnormal plasma a plot of change of optical density with time versus time at a wavelength effective for detecting the cleaved chromophore. The Figure clearly illustrates the substantial elimination of the lag time for both normal and abnormal plasma. The lengthened prothrombin time of the abnormal plasma is evidenced by the lowered slope of the curve. Using the expression $e^{at}$, the slopes (a) of the curves for the normal and the abnormal plasma may be calculated and correlated with the conventionally-determined prothrombin time using the standard curve of FIG. 4.

The present method also makes possible for the first time a method for determining the rate of thrombin production based upon from one to three determinations of optical density change with time at specified times. Such determinations, exemplified by the single determination at time "T" in FIG. 6, evaluate equivalent moments in the thrombin generation process for both normal and abnormal plasma (including those from fibrinogen-deficient individuals), since the lag time for both has been diminished to approximately the same small value by the use of the "serum reagent." The determination of the change of optical density with time at this specified time is therefore directly related to the slope of the curve and hence by suitable calculation to the rate of thrombin generation.

Figure 7:
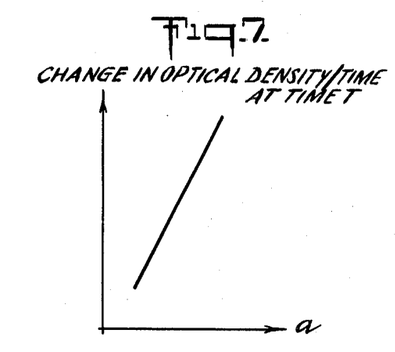
FIG. 7 represents a plot of change in optical density ($\Delta$OD) with time vs a at a given time.

A correlation curve between the optical density change with time ($\Delta OD/t$) and exponential rate of thrombin generation (a) at a particular time T is illustrated by FIG. 7. Once such a curve is established by plotting $\Delta OD/t$ against a for various plasma samples at time T, the curve may be used to determine the slope "a" for an unknown plasma sample by determining only a single $\Delta OD/t$ at time T and a wavelength effective for detecting the cleaved chromophore of the chromogenic substrate. It is contemplated that from one to three such determinations may be required to obtain accurate results.

Figure 8:
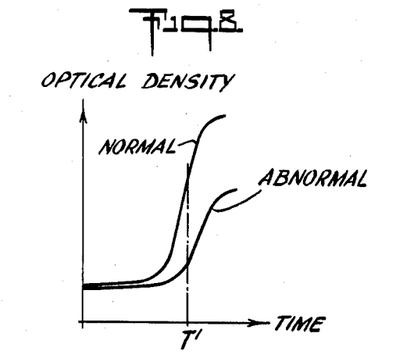
FIG. 8 represents a plot of optical density vs time for the present method.

A determination of the rate of thrombin production may also be obtained based upon one to three optical density measurements at specified times. Such measurements, exemplified by the single measurement at time "T'" in FIG. 8, also evaluate equivalent moments in the thrombin generation process for both normal and abnormal plasmas (including those from fibrinogen-deficient individuals), since the lag time for both has been diminished to approximately the same small value by the use of the serum reagent. The optical density measurement at this specified time is therefore directly related to the slope of the curve and hence by suitable calculation to the rate of thrombin generation.

Figure 9:
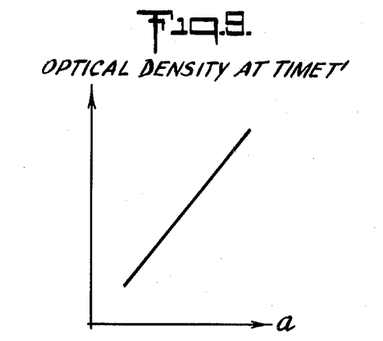
FIG. 9 represents a plot of optical density vs a at a given time.

A correlation curve between optical density and exponential rate of thrombin generation (a) at time T' is illustrated in FIG. 9. Once such a curve is established by plotting optical density against a for various plasma samples at time T', the curve may be used to determine the slope "a" for an unknown plasma sample by measuring only a single optical density value at time T' and a wavelength effective for detecting the cleaved chromophore of the chromogenic substrate. It is contemplated that from one to three such determinations may be required to obtain accurate results.

The chromogenic substrate may be any material which releases a chromophore when cleaved by thrombin and is substantially specific for thrombin among the other materials present in the blood. A preferred chromogenic substrate is a member selected from the group consisting of D-phenylalanyl-L-pipecolyl-L-arginyl-para-nitroanilide and its acid addition salts. The dihydrochloride salt of this substrate is sold by Ortho Diagnostics, Inc., under the designation S-2238. A convenient wavelength for the detection of the cleaved chromophore of this chromogenic substrate is 405 nm. However, it is within the scope of the present invention to employ any other effective chromogenic substrate, such as that sold by Ortho Diagnostics, Inc. under the designation S-2160, which is benzyl-L-phenylalanyl-L-valyl-L-arginyl-para-nitroanilide hydrochloride, or that sold by Pentapharm (a division of Boehringer Mannheim) under the designation Chromozyme TH, which is tosyl-glycol-L-prolyl-L-arginyl-para-nitroanilide.

Chromogenic substrates having a variety of chromophores and fluorophores attached thereto are described in (e.g.) U.S. Pat. Nos. 3,884,896; 3,886,136; and 4,061,625, which are incorporated herein by reference. These U.S. patents disclose substrates which are useful for detection of thrombin by absorbence or fluorescence spectrophotometry.

The thromboplastin may be from any source desired, although Ortho Brain Thromboplastin sold by Ortho Diagnostics, Inc., is preferred. It is recognized that different samples of thromboplastin sold by different manufacturers may not be identical in their biological response and that measurements obtained using thromboplastin from one commercial source may not be identical with those made using thromboplastin from a different commercial source. Nevertheless, the subject method will function equally well regardless of the source of the thromboplastin. The preparation of thromboplastin is disclosed in, e.g., *Hemorrhagic Diseases* by Armand J. Quick, Lea and Febiger, Philadelphia, 1957, pp 375–378.

The preparation of the serum reagent has been discussed adequately above. The serum (containing serum reagent) may be diluted to the appropriate concentration with, e.g., 0.9% saline.

The test plasma is prepared in the normal fashion known in the art and is treated with citric acid to sequester any free calcium ions and thus prevent clotting until the commencement of the test.

The method should be practiced at a known and controlled temperature in order for results to be comparable, but the actual temperature used is not critical. The temperature of 37° C. is one commonly used in biological laboratories and thus is conveniently selected for the practice of the present method.

The method is preferably practiced at a pH which is optimum for cleavage of the particular chromophore and substrate, to which end buffers are employed to maintain the optimum pH as recognized in the art. A convenient buffer for use with the S-2238 chromogenic substrate to maintain a pH of about 8.5 is TRIS (conveniently in saline solution), which is tris(hydroxymethyl)aminomethane, but other buffers such as EPPS (N-2-hydroxyethylpiperazine-N'-3-propanesulfonic acid), TRICINE[N-tris(hydroxymethyl)methylglycine], BICINE[N,N-bis(2-hydroxyethyl)glycine], glycylglycine, and the like, may be used. Other buffers having different $pK_a$ values may be preferred for other chromogenic substrates.

The method is preferably practiced at an ionic strength which is optimum for cleavage of the particular chromophore and substrates to which end various salts (e.g., sodium chloride) are employed to regulate the ionic strength as recognized in the art. For the S-2238 chromogenic substrate, the ionic strength of the buffer solution is preferably about 0.15, although variation from this value may be made.

In this preferred embodiment of the present invention, the chromogenic substrate should be present in a concentration sufficient to allow detection of the cleaved chromophore. The upper limit of concentration for the chromogenic substrate is simply the solubility of the substrate in the mixture of ingredients. It is preferred that the chromogenic substrate be present in stoichiometric excess compared to the amount of plasma so that the substrate concentration will not limit the rate of the reaction.

The amount of thromboplastin may vary from the minimum amount required for thrombin production up to the amount which inhibits such production. It has been found that from 0.15 ml to about 0.40 ml of Ortho Brain Thromboplastin can be used for a 0.05 ml sample of plasma, which relative amount is preferred, but it is contemplated that the relative amount of thromboplastin could be varied more widely without departing from the teachings of the present invention.

While Ortho Brain Thromboplastin is a commercial product sold by Ortho Diagnostics, Inc., and contains calcium ion within it already in a concentration of 0.01 M, it should clearly be understood that the concentration of calcium ion may be varied independently.

The concentration of test plasma may vary between the lower limit at which no response is observed and the upper limit at which the clotting causes turbidity which interferes with the measurement of thrombin production by whatever means used. Conveniently, 0.05 ml of test plasma may be used in a total volume of reagents of 2.1 ml, but clearly considerable variations may be made in this concentration while still remaining within the scope of the present invention.

The concentration of serum reagent in the reaction mixture should be such as to reduce to a minimum the lag time before the production of significant amounts of thrombin begins for both normal and abnormal plasma. This threshold amount of serum reagent may easily be determined for various concentrations of other reagents. It has been found that equal parts of diluted serum reagent (composed of one part serum reagent and 1.5 parts 0.9% saline solution) and plasma is particularly effective, but considerable variation from this relative concentration is allowed. It should be noted, however, that the serum reagent as obtained by at least one of the methods described above contains unactivated Factor X as well as unactivated Factor V, which factors could distort the results of this test method if present in too high a concentration. The risk of such distortion can be minimized by removal of such unwanted factors, e.g., by adsorption with barium chloride. Such effects can easily be monitored by performing the subject method while holding all variables constant except the concentration of serum reagent. The range of serum reagent concentration within which reproducible results are obtained can thus clearly be determined.

The functional criteria for the preferred conditions for the present method are the following:
(a) the dilution curve given in FIG. 5 should be linear; and
(b) a sharp increase in thrombin production detectable by the method used should be produced as shown in FIG. 2.

Within these two preferred criteria, the concentrations of the reagents may be varied.

The present method is illustrated by the following examples, which are given by way of illustration and not to limit the scope of the present invention.

EXAMPLE I

The serum reagent is prepared as follows:
Reagents:
  Human Plasma (anticoagulated with Sodium Citrate)
  Calcium Chloride solution—0.28 M in deionized water
  Ortho Brain Thromboplastin (OBT) (Containing 0.01 M calcium ion)
  Barium Chloride solution—1.0 M in deionized water

A. Formation of Serum

OBT was reconstituted according to manufacturer's directions. (If more than one vial of OBT is required, the contents of the vials are pooled prior to use.) The plasma, calcium chloride solution and OBT were cooled +5° C. The following proportions of reagents were then combined in an appropriate container:
  9 parts plasma
  0.33 parts calcium chloride solution
  0.67 parts OBT The calcium chloride solution and OBT were added rapidly to the plasma, and the resultant mixture is stirred several times to insure homogeneous dispersion of reagents. The mixture was kept at +5° C. for two hours after the plasma had clotted. The clotted plasma was then transferred to container(s) suitable for centrifugation and centrifuged at 5000 g for 15 minutes at +5° C. The supernatant serum, which contains the serum reagent, was decanted and retained, while the compacted fibrin clot was discarded. The supernatant serum may then be used or may be frozen ($-70°$ C.) or lyophilized for storage. Lyophilized serum is reconstituted to the original volume prior to use.

B. Adsorption of Serum Reagent

The following proportions of reagents were combined in an appropriate container:
  10 parts Serum Reagent (at +5° C.)
  1 part barium chloride solution The barium chloride solution was added slowly to the serum. After all of the barium chloride had been added, the mixture was stirred gently in order to insure dispersion of reagents. The adsorption mixture was then kept at +5° C. for 15 minutes. The adsorbed serum was transferred to container(s) suitable for centrifugation, and the mixture was centrifuged at 3000 g for 30 minutes at +5° C. The supernatant, containing the serum reagent, was carefully poured off and retained, while the precipitate was discarded. The supernatant adsorbed serum may then be used or may be frozen ($-70°$ C.) or lyophilized for storage. This adsorption procedure removes certain unwanted serum components.

EXAMPLE II

The serum reagent was also prepared as follows:
Reagents:
  9 parts human plasma
  0.67 parts of 0.15 M calcium chloride solution
  0.33 parts Activated Thrombofax All reagents were cooled to 5° C. prior to use. The reagents were mixed and kept at 5° C. until clotting had occurred, which may be as long as several hours, depending upon the volume used. The clotted plasma was then centrifuged and treated as described in Example I for the clotted plasma formed therein.

EXAMPLE III

The following reagents are prepared:
(1) S-2238/buffer: one part S-2238 chromogenic substrate (2 mM in deionized water) is mixed with 5.4 parts of 0.05 M TRIS buffer in saline having a pH of 8.5 and an ionic strength (I) of 0.15.
(2) Ortho Brain Thromboplastin (containing 0.01 M calcium ion).
(3) diluted serum reagent: one part unadsorbed serum prepared in Example IA is combined with 1.5 parts of 0.9% saline solution.

(4) test plasma or control plasma.

The following volumes of reagents are added to a 12×75 mm polystyrene test tube at 37° C.:
1.60 ml S-2238/buffer (37° C.)
0.40 ml Ortho Brain Thromboplastin (37° C.)
0.05 ml diluted serum reagent
0.05 ml test plasma or control plasma The reagents are mixed and immediately aspirated into a flow-through cell thermostatted at 37° C. Absorbance measurements at 405 nm are automatically relayed from the spectrophotometer to a statistical calculator. A simultaneous recording of absorbance with respect to time is obtained from the spectrophotometer strip chart recorder, while a graphical representation of the change in slope of the absorbance curve with respect to time is obtained from the statistical calculator. The change in absorbance is calculated over every five-second period of reaction time. The plot of change in slope of the absorbance curve with respect to time resembles FIG. 3, except that the portion to the right of P or P' may vary depending upon the degree of excess of chromogenic substrate used and the limits of the instrument used. The exponential rate of thrombin generation (a) is then obtained by performing an exponential regression between time (the mid-point of each 5-second interval) and the natural logarithm of the change in absorbance with respect to time.

Figure 10:
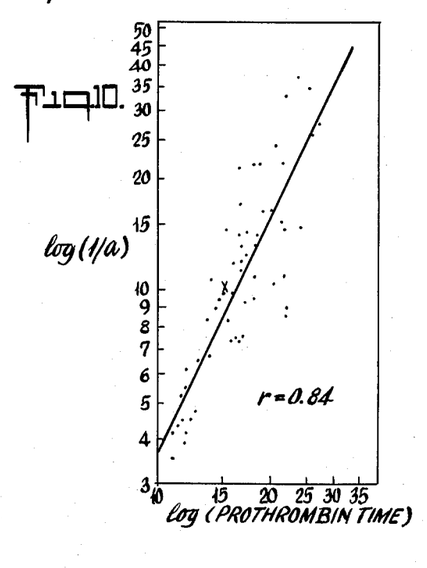
FIG. 10 represents a plot of (1/a) on a log scale vs (t) on a log scale for a group of 62 plasma samples.

This method was repeated with 61 other samples of plasma having varying degrees of abnormality. The one-stage prothrombin times for these 62 plasma samples were determined using conventional techniques, and a plot was prepared similar to FIG. 4 to correlate these slope values with observed prothrombin times. This correlation diagram is shown herein as FIG. 10, which has a correlation coefficient (r) equal to 0.84.

In the above Examples and throughout the specification, parts are by volume unless otherwise indicated.

These Examples have been given by way of illustration only and not to limit the scope of the present invention, which scope is defined in the following claims.

What is claimed is:

1. A method for determining, for a fibrinogen-normal individual, the effectiveness of that portion of the blood clotting mechanism measured by a conventional one-stage prothrombin time test which comprises the steps of:
   (a) determining the exponential rate of thrombin formation in a mixture comprising effective thrombin-forming concentrations of thromboplastin, calcium ion, and test plasma from said individual; and
   (b) comparing this determined rate to a compilation of rates for plasmas of known clotting properties.

2. The method of claim 1 wherein said mixture further comprises an effective lag-time-reducing concentration of serum reagent or thrombin.

3. The method of claim 1 wherein a chromogenic substrate specific for thrombin is used to determine the exponential rate of thrombin formation.

4. A method for determining, for a fibrinogen-normal individual, the effectiveness of that portion of the blood clotting mechanism measured by a conventional one-stage prothrombin time test which comprises the steps of:
   (a) combining effective concentrations of a chromogenic substrate specific for thrombin, thromboplastin, calcium ion, serum reagent, and test plasma from said individual at a controlled temperature, pH, and ionic strength to form a mixture;
   (b) measuring the change with time in absorbance of said mixture at a wavelength effective for detecting the cleaved chromophore of the chromogenic substrate;
   (c) plotting the change with time in absorbance measured in step (b) against time;
   (d) calculating the exponential rate of thrombin formation (a) from the plot in step (c) according to the formula $e^{at}$; and
   (e) comparing the calculated rate to a compilation of rates for plasmas of known clotting properties.

5. The method of claim 4 wherein the chromogenic substrate is D-phenylalanyl-L-pipecolyl-L-arginyl-para-nitroanalide, and the acid addition salts thereof; the serum reagent is produced by treating citrated human plasma with effective clotting concentrations of calcium ion and thromboplastin and isolating the supernatant serum containing the serum reagent; the pH of the mixture is about 8.5; and the wavelength for detecting the cleaved chromophore is about 405 nm.

6. The method of claim 4 wherein the chromogenic substrate is D-phenylalanyl-L-pipecolyl-L-arginyl-para-nitroanalide dihydrochloride; the thromboplastin is Ortho Brain Thromboplastin (containing 0.01 M calcium ion) and is present in a volume of from about three to about eight times the volume of plasma; the serum reagent is produced by treating citrated human plasma with effective clotting concentrations of calcium ion and thromboplastin and isolating the supernatant serum containing the serum reagent; the pH of the mixture is about 8.5; the temperature of the mixture is about 37° C.; and the wavelength for detecting the cleaved chromophore is about 405 nm.

7. A method for determining the one-stage prothrombin time for a fibrinogen-normal individual which comprises the steps of:
   (a) determining the exponential rate of thrombin formation in a mixture comprising effective thrombin-forming concentrations of thromboplastin, calcium ion, and test plasma from said individual; and
   (b) calculating the one-stage prothrombin time from said determined rate by use of a standard curve correlating the exponential rate of thrombin formation and the one-stage prothrombin time.

8. The method of claim 7 wherein said mixture further comprises an effective lag-time-reducing concentration of serum reagent or thrombin.

9. The method of claim 7 wherein a chromogenic substrate specific for thrombin is used to determine the exponential rate of thrombin formation.

10. A method for determining the one-stage prothrombin time for a fibrinogen-normal individual which comprises the steps of:
   (a) combining effective concentrations of a chromogenic substrate specific for thrombin, thromboplastin, calcium ion, serum reagent, and test plasma from said individual at a controlled temperature, pH, and ionic strength to form a mixture;
   (b) measuring the change with time in absorbance of said mixture at a wavelength effective for detecting the cleaved chromophore of the chromogenic substrate;
   (c) plotting the change with time in absorbance measured in step (b) above against time;
   (d) calculating the exponential rate of thrombin formation (a) from the plot in step (c) above according to the formula $e^{at}$; and (e) determining the one-stage prothrombin time for said plasma by comparing the calculated rate obtained in step (d) above to a standard curve relating exponential rate of thrombin formation and one-stage prothrombin time.

11. The method of claim 10 wherein the chromogenic substrate is D-phenylalanyl-L-pipecolyl-L-arginyl-para-nitroanalide, and the acid addition salts thereof; the serum reagent is produced by treating citrated human plasma with effective clotting concentrations of calcium ion and thromboplastin and isolating the supernatant serum containing the serum reagent; the pH of the mixture is about 8.5; and the wavelength for detecting the cleaved chromophore is about 405 nm.

12. The method of claim 10 wherein the chromogenic substrate is D-phenylalanyl-L-pipecolyl-L-arginyl-para-nitroanalide dihydrochloride; the thromboplastin is Ortho Brain Thromboplastin (containing 0.01 M calcium ion) and is present in a volume of from about three to about eight times the volume of plasma; the serum reagent is produced by treating citrated human plasma with effective clotting concentrations of calcium ion and thromboplastin and isolating the supernatant serum containing the serum reagent; the pH of the mixture is about 8.5; the temperature of the mixture is about 37° C.; and the wavelength for detecting the cleaved chromophore is about 405 nm.

13. A method for determining the exponential rate of thrombin formation for an individual which comprises the steps of:
(a) combining effective concentrations of a chromogenic substrate specific for thrombin, thromboplastin, calcium ion, serum reagent, and test plasma from said individual at a controlled temperature, pH, and ionic strength to form a mixture;
(b) measuring the change with time in absorbance of said mixture at a wavelength effective for detecting the cleaved chromophore of the chromogenic substrate;
(c) plotting the change with time in absorbance measured in step (b) against time; and
(d) calculating the exponential rate of thrombin formation (a) from the plot in step (c) according to the formula $e^{at}$.

14. The method of claim 13 wherein the chromogenic substrate is D-phenylalanyl-L-pipecolyl-L-arginyl-para-nitroanalide, and the acid addition salts thereof; the serum reagent is produced by treating citrated human plasma with effective clotting concentrations of calcium ion and thromboplastin and isolating the supernatant serum containing the serum reagent; the pH of the mixture is about 8.5; and the wavelength for detecting the cleaved chromophore is about 405 nm.

15. The method of claim 13 wherein the chromogenic substrate is D-phenylalanyl-L-pipecolyl-L-arginyl-para-nitroanalide dihydrochloride; the thromboplastin is Ortho Brain Thromboplastin (containing 0.01 M calcium ion) and is present in a volume of from about three to about eight times the volume of plasma; the serum reagent is produced by treating citrated human plasma with effective clotting concentrations of calcium ion and thromboplastin and isolating the supernatant serum containing the serum reagent; the pH of the mixture is about 8.5; the temperature of the mixture is about 37° C.; and the wavelength for detecting the cleaved chromophore is about 405 nm.

16. A method for determining the exponential rate of thrombin formation for an individual in thromboplastin-treated, recalcified plasma which comprises the steps of:
(a) combining effective concentrations of a chromogenic substrate specific for thrombin, thromboplastin, calcium ion, serum reagent, and test plasma from said individual at a controlled temperature to form a mixture;
(b) measuring at from one to three specified times the change with time in absorbance of said mixture at a wavelength effective for detecting the cleaved chromophore of the chromogenic substrate; and
(c) estimating the exponential rate of thrombin formation by comparing the change with time in absorbance at each specified time measured in step (b) above to a standard curve relating the change with time in absorbance at each such specified time and the exponential rate of thrombin formation.

17. The method of claim 16 wherein the chromogenic substrate is D-phenylalanyl-L-pipecolyl-L-arginyl-para-nitroanalide, and the acid addition salts thereof; the serum reagent is produced by treating citrated human plasma with effective clotting concentrations of calcium ion and thromboplastin and isolating the supernatant serum containing the serum reagent; the pH of the mixture is about 8.5; and the wavelength for detecting the cleaved chromophore is about 405 nm.

18. The method of claim 16 wherein the chromogenic substrate is D-phenylalanyl-L-pipecolyl-L-arginyl-para-nitroanalide dihydrochloride; the thromboplastin is Ortho Brain Thromboplastin (containing 0.01 M calcium ion) and is present in a volume of from about three to about eight times the volume of plasma; the serum reagent is produced by treating citrated human plasma with effective clotting concentrations of calcium ion and thromboplastin and isolating the supernatant serum containing the serum reagent; the pH of the mixture is about 8.5; the temperature of the mixture is about 37° C.; and the wavelength for detecting the cleaved chromophore is about 405 nm.

19. A method for determining the exponential rate of thrombin formation for an individual in thromboplastin-treated, recalcified plasma which comprises the steps of:
(a) combining effective concentrations of a chromogenic substrate specific for thrombin, thromboplastin, calcium ion, serum reagent, and test plasma from said individual at a controlled temperature to form a mixture;
(b) measuring at from one to three specified times the absorbance of said mixture at a wavelength effective for detecting the cleaved chromophore of the chromogenic substrate; and
(c) estimating the exponential rate of thrombin formation by comparing the absorbance at each specified time measured in step (b) above to a standard curve relating the absorbance at each such specified time and the exponential rate of thrombin formation.

20. The method of claim 19 wherein the chromogenic substrate is D-phenylalanyl-L-pipecolyl-L-arginyl-para-nitroanalide, and the acid addition salts thereof; the serum reagent is produced by treating citrated human plasma with effective clotting concentrations of calcium ion and thromboplastin and isolating the supernatant serum containing the serum reagent; the pH of the mixture is about 8.5; and the wavelength for detecting the cleaved chromophore is about 405 nm.

21. The method of claim 19 wherein the chromogenic substrate is D-phenylalanyl-L-pipecolyl-L-arginylpara-nitroanalide dihydrochloride; the thromboplastin is Ortho Brain Thromboplastin (containing 0.01 M calcium ion) and is present in a volume of from about three to about eight times the volume of plasma; the serum reagent is produced by treating citrated human plasma with effective clotting concentrations of calcium ion and thromboplastin and isolating the supernatant serum containing the serum reagent; the pH of the mixture is about 8.5; the temperature of the mixture is about 37° C.; and the wavelength for detecting the cleaved chromophore is about 405 nm.

* * * * *